(12) United States Patent
van Gool

(10) Patent No.: US 8,660,624 B2
(45) Date of Patent: Feb. 25, 2014

(54) DETERMINATION OF THE STATE OF HEALTH OF A HUMAN BEING

(76) Inventor: Albert van Gool, Enschede (NL)

( * ) Notice: Subject to any disclaimer, the term of this patent is extended or adjusted under 35 U.S.C. 154(b) by 1329 days.

(21) Appl. No.: 11/887,033

(22) PCT Filed: Mar. 22, 2006

(86) PCT No.: PCT/NL2006/000151
§ 371 (c)(1), (2), (4) Date: Jul. 28, 2008

(87) PCT Pub. No.: WO2006/101389
PCT Pub. Date: Sep. 28, 2006

(65) Prior Publication Data
US 2009/0062631 A1    Mar. 5, 2009

(30) Foreign Application Priority Data
Mar. 24, 2005 (NL) .................................. 1028619

(51) Int. Cl.
*A61B 5/00* (2006.01)

(52) U.S. Cl.
USPC .......................................................... 600/310

(58) Field of Classification Search
USPC .................. 600/310, 316, 342, 345–347, 362; 356/450
See application file for complete search history.

(56) References Cited

U.S. PATENT DOCUMENTS

| | | | |
|---|---|---|---|
| 5,377,008 A | 12/1994 | Ridgway et al. | |
| 5,804,453 A * | 9/1998 | Chen | 436/518 |
| 6,429,023 B1 | 8/2002 | Gharavi | |
| 6,618,536 B1 | 9/2003 | Heideman et al. | |
| 7,184,148 B2 * | 2/2007 | Alphonse | 356/479 |
| 7,394,547 B2 * | 7/2008 | Tan et al. | 356/480 |
| 7,931,592 B2 * | 4/2011 | Currie et al. | 600/309 |
| 2003/0008407 A1 | 1/2003 | Fu | |
| 2003/0050543 A1 | 3/2003 | Hartmann | |
| 2004/0199060 A1 * | 10/2004 | Oshima et al. | 600/310 |
| 2004/0254438 A1 | 12/2004 | Chuck et al. | |
| 2005/0010090 A1 | 1/2005 | Acosta et al. | |

FOREIGN PATENT DOCUMENTS

WO    2005/001447 A1    1/2005

* cited by examiner

*Primary Examiner* — Max Hindenburg
(74) *Attorney, Agent, or Firm* — The Webb Law Firm

(57) ABSTRACT

The invention provides a method for the determination of the state of an entity, in particular the state of health of a human being or animal. The method includes the step of contacting secreted compounds or related reaction products with a surface linked to an optical waveguide in such a way that compounds binding to the surface can influence the propagation of light in the waveguide, determining the occurring influence by means of an optical interferometric measuring principle, and deducing the state from the occurring influence. The invention further provides a device for the determination of such a state.

13 Claims, 2 Drawing Sheets

DETERMINATION OF THE STATE OF HEALTH OF A HUMAN BEING

FIELD OF THE INVENTION

The invention concerns the determination of the state of an entity, in particular the state of health of a human being or animal, more in particular the diabetic condition.

BACKGROUND OF THE INVENTION

In US2003/0008407 a non-invasive diagnostic system is described for monitoring the condition of an entity, e.g. the diabetic condition of a human being or animal. In this system a number of volatile or gaseous compounds secreted by the entity or body that characterize the condition or state are determined. The obtained data are processed in such a way that conclusions may be drawn concerning the condition or state.

An important application is to monitor human beings with diabetes mellitus, diabetes for short, a chronic disorder of the glucose metabolism in the body. Because the pancreas, that produces the hormone insulin that controls the uptake of glucose in cells, does not work or works insufficiently, blood glucose is not absorbed adequately or at all. People suffering from diabetes have an increased risk of cardiovascular diseases, high blood pressure, neurological disorders, skin disorders, deterioration of the retina, kidney disorders and impotence to name but a few, which can lead to serious debilitation and in extreme cases to an early death. The number of diabetics worldwide is estimated at 100-150 million and the number of people diagnosed with diabetes has increased rapidly over the past decades from 2-3% to 5-6%.

As yet there is no cure for diabetes, but the above complications can be prevented or at least reduced or postponed to a considerable extent by an adequate control of the blood glucose level. This can be done by medicinal treatment or administration of insulin in combination with a suitable diet and lifestyle. A good—in ideal cases a continuous—control of blood glucose levels is of prime importance. Ideally values of between 4 and 10 mmole/l (the extreme values of a non-diabetic person) should be maintained.

In US2003/0008407 only a limited number of known possible sensors and detection facilities are cited briefly—an oscillator, a sensor based on electrical conductivity and traditional HPLC, GC or MS methods.

US 2005/0010090 provides a more extensive overview of known methods and techniques to determine blood glucose levels. Here a distinction is made between methods referred to as 'traditional invasive', 'alternative invasive', 'non-invasive' and 'implantable' and techniques such as 'direct' and 'indirect' glucose measurement. In a traditional invasive method a sample of arterial or venous blood is drawn by means of a needle, or a capillary blood sample is taken by means of a lancet. However, this method is considered to be inconvenient and piercing the skin is painful. Also the analysis of the sample thus obtained yields only a random indication. As has been said before, an adequate control of blood glucose levels requires a continuous or at least frequent (during night and day) measurement. It will be obvious that this entails unacceptable stress for the patient and is practically impossible to implement.

In an alternative invasive method the alternative can refer to the site where the sample is taken but often it refers to an alternative way to draw a sample of interstitial fluid, blood or a mixture of both. This can be done by (i) piercing the skin with a laser, (ii) to enhance the permeation of interstitial fluid through the skin electrically, or (iii) to locally apply a reduced pressure to the skin in order to stimulate the permeation of interstitial fluid through the skin. To determine the glucose levels in the obtained biological samples spectrophotometrical methods (Raman, fluorescence, visible light, UV and IR) are used besides electrochemical, (electro)enzymatic or colorimetrical methods. The glucose levels can be determined directly or indirectly via a number of compounds that characterise the glucose level or diabetic condition. In practice, such known methods and techniques turn out to be relatively laborious and difficult to perform by a layman, insufficiently fast or accurate, often are insufficiently reliable, often costly and unsuitable for (semi)-continuously or automatically measuring the blood glucose levels. To date, the cited shortcomings prevent a (widespread) application of these techniques. In a non-invasive method no sample is taken but a physiological parameter is determined by studying an area of the body and through a certain algorithm the glucose level in the blood is deduced. In many cases a form of spectroscopy is used, but thermal or electrical methods are used as well. Such known techniques again prove to be fairly laborious, difficult to perform by a layman, and expensive. Consequently non-invasive methods based on the mentioned techniques are not applied (on a wider scale).

Furthermore a number of types of short-term or long term implantable glucose sensors are under development. U.S. Pat. No. 5,377,008 and U.S. Pat. No. 6,429,023 describe optical devices for determining characteristics of liquids, based on a sensor surface linked to a (Mach-Zehnder) interferometer. U.S. Pat. No. 6,618,536 describes a similar device with which in principle all kinds of parameters such as air humidity, chemical composition of gases or liquids and variations in optical refraction index and temperature can be measured. Such devices prove to be very sensitive with very low detection limits. Moreover, they can be made to be selective for one or more specific compounds.

It can be concluded that there is very big need for an affordable, user-friendly system with which the state of health, in particular the diabetic condition of a human can be determined continuously, or at least a sufficient number of times a day, pain-free or at least with minimal stress, sufficiently precise and preferably automatically. In practice none of the known systems, methods and techniques fulfils this need. The purpose of the invention is to provide such a system.

SUMMARY OF THE INVENTION

Figure 1:
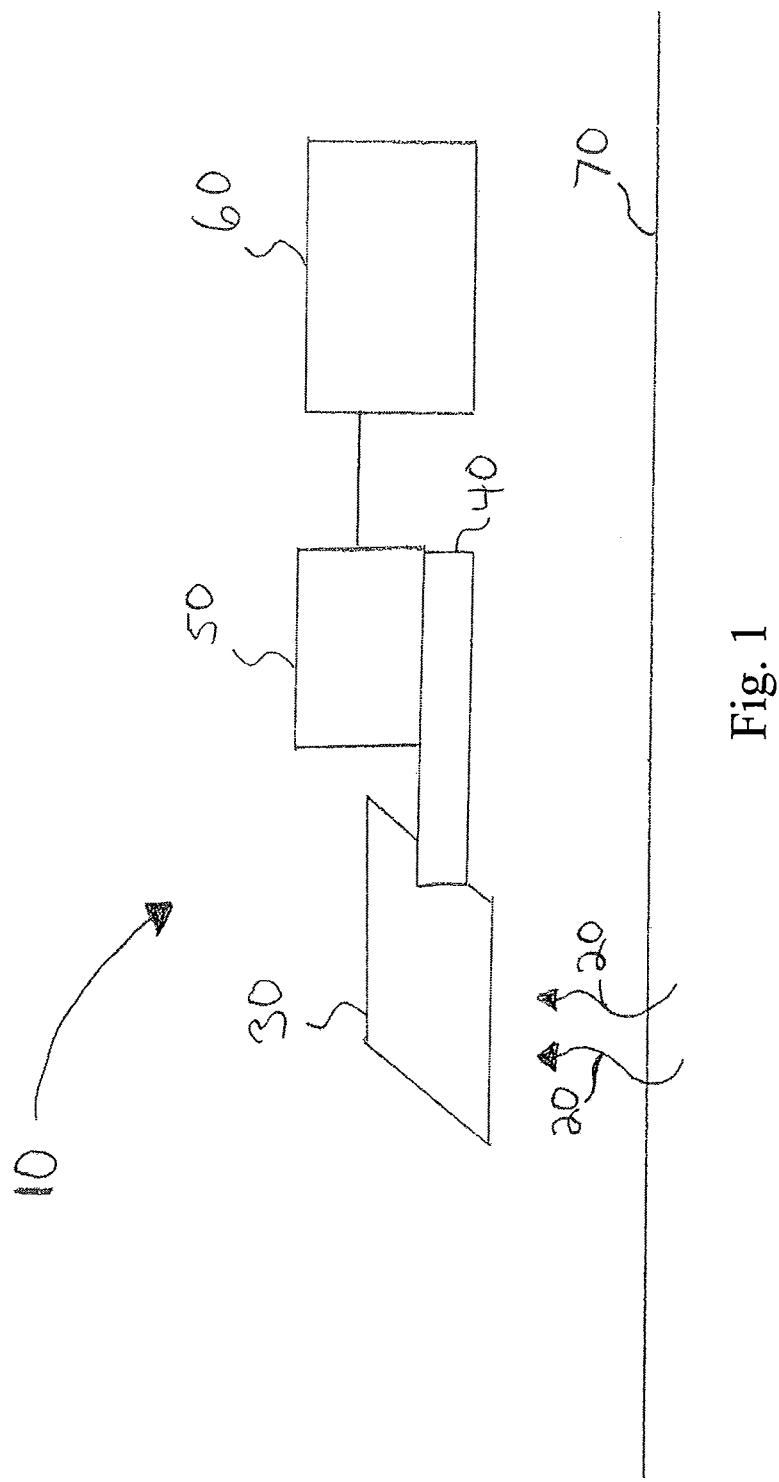
FIG. 1 shows an embodiment of the device for determination of the state of health of a human being or animal according to a non-limiting embodiment of the present invention.

To this end, the invention provides a system 10 as represented in FIG. 1 for the determination of the state of an entity, in particular the health of a human being or animal, comprising: contacting secreted compounds 20 or corresponding reaction products with a surface 30 provided to this end, the surface 30 being linked to an optical waveguide 40 in such a way that compounds binding to the surface 30 can influence the propagation of light in the waveguide 40; determining the occurring influence by means of an interferometric measuring principle using an optical interferometer 50; and means 60 for deducing the state from the occurring influence.

In the framework of the invention, 'to secrete' is intended to mean 'secretion by the entity', in particular 'secretion by the body of the humans being or the animal without a traditional invasive measure'. By 'determining the state (of health)' it is meant in the present invention 'at least partially determining the state (of health)'.

The secreted compounds 20 can be secreted by the skin 70 in either liquid or gaseous form, possibly dissolved in e.g. sweat or interstitial fluid of mixed with air or as an aerosol, but also by the lungs in the shape of gases or liquid droplets present in the exhaled air. In a preferred embodiment, the state is the diabetic condition and the secreted compounds 20 characterize the diabetic condition.

Evidently, several surfaces 30 can be applied, linked to one or more interferometric systems 40, 50. In this case, each surface 30 can be more or less selective for one or more specific compounds 20, or one or more reference measurements can be performed.

Such a system 10 can be made affordable and user-friendly. This way the condition of an entity, in particular the state of health, more in particular the diabetic condition of a human being or animal can be determined pain-free or at least with minimal stress, sufficiently precise, possibly automatically, possibly continuously or at least a sufficiently large number of times per unit of time.

Figure 2:
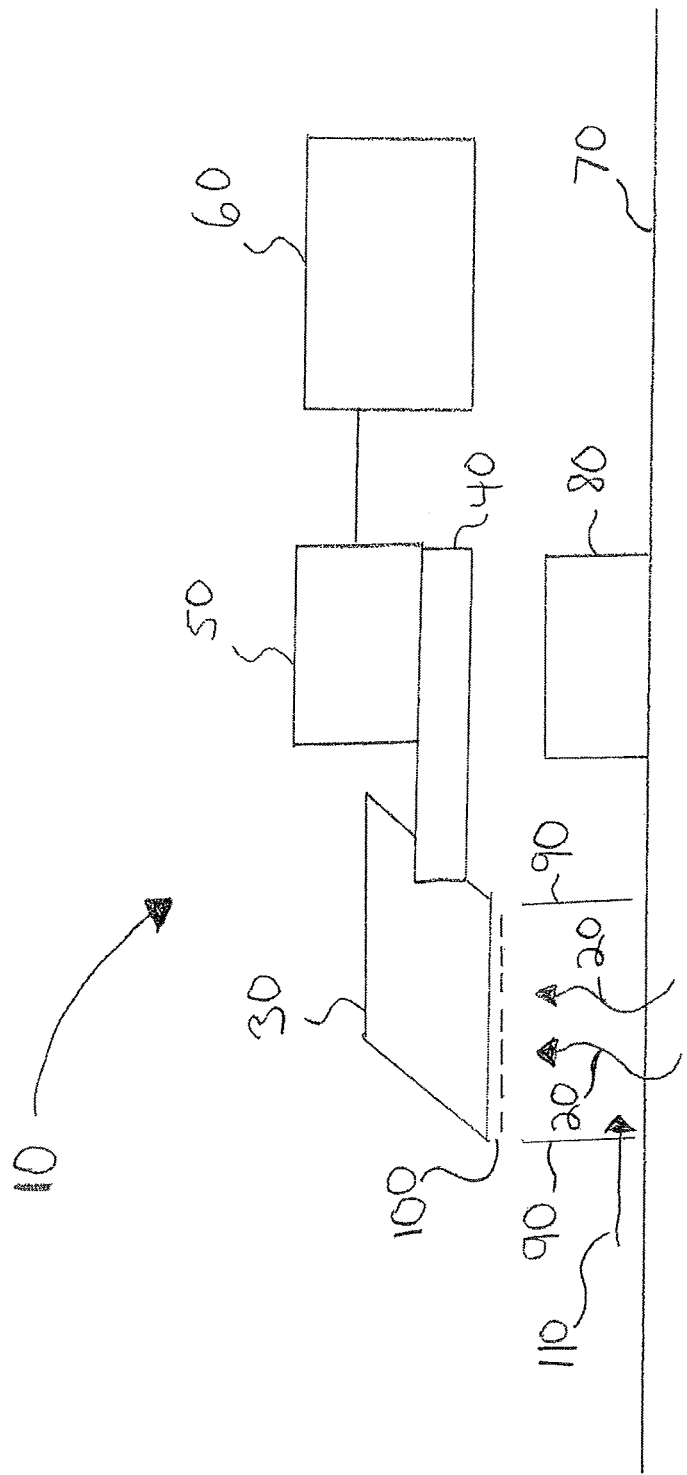
FIG. 2 shows an additional embodiment of the device for determination of the state of health of a human being or animal according to a non-limiting embodiment of the present invention.

As shown in FIG. 2, the system 10 can also comprise means 80 for the stimulation of the secretion of compounds 20. E.g. the permeation of compounds 20 through the skin 70 can be stimulated electrically or thermally or by applying a reduced pressure.

The system 10 can also comprise means 90 for guiding the secreted compounds 20 or related reaction products to the surface 30. In this case adjuvants or reagents like oxygen 110 can also be added.

The system can also comprise the selective permeation of secreted compounds or related reaction products, e.g. by means of one or more suitable selectively permeable membranes or filters 100. The system 10 can also comprise the selective binding of the secreted compounds 20 or related reaction products to the surface 30, so only the desired specific compound or compounds are bonded to the surface 30. This way the system 10 can be made to be more selective, undesirable polluting or interfering compounds are removed and the sensitivity, accuracy and reproducibility of the system can be increased, as well as its life-span.

The invention claimed is:

1. A method for the determination of the state of health of a human being or animal, comprising the steps of:
    contacting secreted compounds or related reaction products with a surface, the surface being linked to an optical waveguide in such a way that compounds binding to the surface can influence the propagation of light in the waveguide;
    determining the occurring influence by means of an optical interferometric measuring principle; and
    deducing, from the occurring influence of the secreted compounds, the state of health of the human being or animal.

2. The method according to claim 1, wherein the secreted compounds are secreted by the skin.

3. The method according to claim 1, wherein the state concerns the diabetic condition and the secreted compounds are characteristic of the diabetic condition.

4. The method according to claim 1, further comprising the step of stimulating the secretion of compounds.

5. The method according to claim 1, further comprising the step of guiding the secreted compounds or related reaction products to the surface.

6. The method according to claim 1, further comprising the step of selectively allowing the permeation of secreted compounds or related reaction products.

7. The method according to claim 1, further comprising the step of selectively binding secreted compounds or related reaction products to the surface.

8. A device for the determination of the state of health of a human being or animal, comprising:
    a surface and an optical waveguide that are linked in such a way that compounds binding to the surface can influence the propagation of light in the waveguide;
    means for bringing secreted compounds or related reaction products in contact with the surface;
    an optical interferometer for the determination of the occurring influence; and
    means for deducing the state of health of the human being or animal from the occurring influence of the secreted compounds.

9. The device according to claim 8, further comprising means for stimulating the secretion of the compounds.

10. The device according to claim 8, further comprising means for guiding secreted compounds or related reaction products to the surface.

11. The device according to claim 8, further comprising means for selectively allowing the permeation of secreted compounds or related reaction products.

12. The device according to claim 8, wherein the surface is able to selectively bind secreted compounds or related reaction products.

13. A method for the determination of the diabetic state in a human or an animal, comprising the steps of:
    contacting secreted compounds or related reaction products with a surface, the surface being linked to an optical waveguide in such a way that compounds binding to the surface can influence the propagation of light in the waveguide;
    determining the occurring influence by means of an optical interferometric measuring principle; and
    deducing, from the occurring influence of the secreted compounds, the diabetic state of the human being or animal.

* * * * *

UNITED STATES PATENT AND TRADEMARK OFFICE
CERTIFICATE OF CORRECTION

PATENT NO. : 8,660,624 B2
APPLICATION NO. : 11/887033
DATED : February 25, 2014
INVENTOR(S) : Albert van Gool It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1757 days.

Signed and Sealed this
Twenty-ninth Day of September, 2015

Michelle K. Lee
*Director of the United States Patent and Trademark Office*